Figure 2:
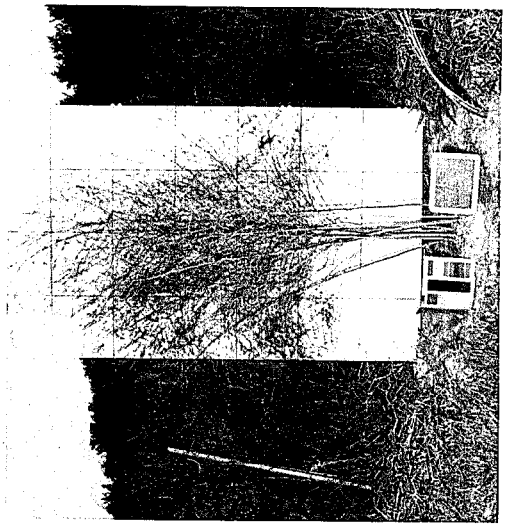

United States Patent [19]

Ellison et al.

[11] Patent Number: Plant 6,969

[45] Date of Patent: Aug. 1, 1989

[54] ASPARAGUS PLANT—'JERSEY TITAN'

[75] Inventors: J. Howard Ellison, Milltown; John J. Kinelski, Princeton, both of N.J.

[73] Assignee: Rutgers University, New Brunswick, N.J.

[21] Appl. No.: 159,684

[22] Filed: Feb. 24, 1988

[51] Int. Cl.[4] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

An Asparagus plant having tolerance to rust (*Puccinia asparagi*), root rot (*Fusarium oxysporum*), and crown rot (*F. monilioforme*), with good vigor and very high branching aspect producing high quality and quantity of marketable yield spears in hot weather, having tips which remain closed when others tend to open prematurely, and having a high rust rating.

1 Drawing Sheet

GENERAL BACKGROUND OF THE DISCLOSURE

This invention relates to Asparagus plants and is directed to an all male hybrid which we have developed and which is one resulting from a long range program devoted to improving Asparagus plants in general and to some particular characteristics thereof.

We have particularly stressed improvement in Asparagus plants for growing in different environments and which are tolerant to rust (*Puccinia asparagi*), root rot (*Fusarium oxysporum*), and crown rot (*F. moniliforme*).

This plant is an example of such improvement and also provides high yield over extended periods of time and trials in at least one area.

DETAILS OF THE INVENTION

Since this new Asparagus plant is vigorous and very high branching, we have chosen to call the same "Jersey Titan" for commercial identification.

Our new cultivar produces spears with tight tips, which remain closed longer than those of other cultivars, thus providing improved spear quality as opposed to spears having loose tips, which are not marketable.

We have asexually propagated this new Asparagus plant by crown division and find that it comes true in successive generations.

In view of our desire to develop plants with improved rust ratings, we have tested this new plant on fusarium infested land and found that as compared with other varieties on a scale of 1 (very rusty) to 9 (healthy) our new cultivar has a rating of 6.6 This may be compared with Mary Washington for example, (an unpatented variety) which has a rust rating of 3, an obviously desirable improvement by "Jersey Titan".

Since our long extending program has required comparison with other varieties and many cultivars of our own development, we have accumulated data to establish and judge the various plants, particularly in respect to marketable yields, establishing annual rankings amoung other facets of comparative data.

This new Asparagus plant while not having the highest marketable yield of an 81 variety line, nevertheless was found to be very high, in fact 3rd in test trials, and is thus superior to many other varieties, some being unpatented such as Martha Washington which on the same scale was nearly 10% less productive.

As a matter of interest, the harvest periods used as basis for establishing the foregoing positions were 21 days in May of one year, (May 7 to May 28) 25 days in May and June (May 13–June 10) 34 days (May 10–June 15) and 45 days (May 2–June 20) of successive years, the averages confirming our before stated relationships.

Figure 1:
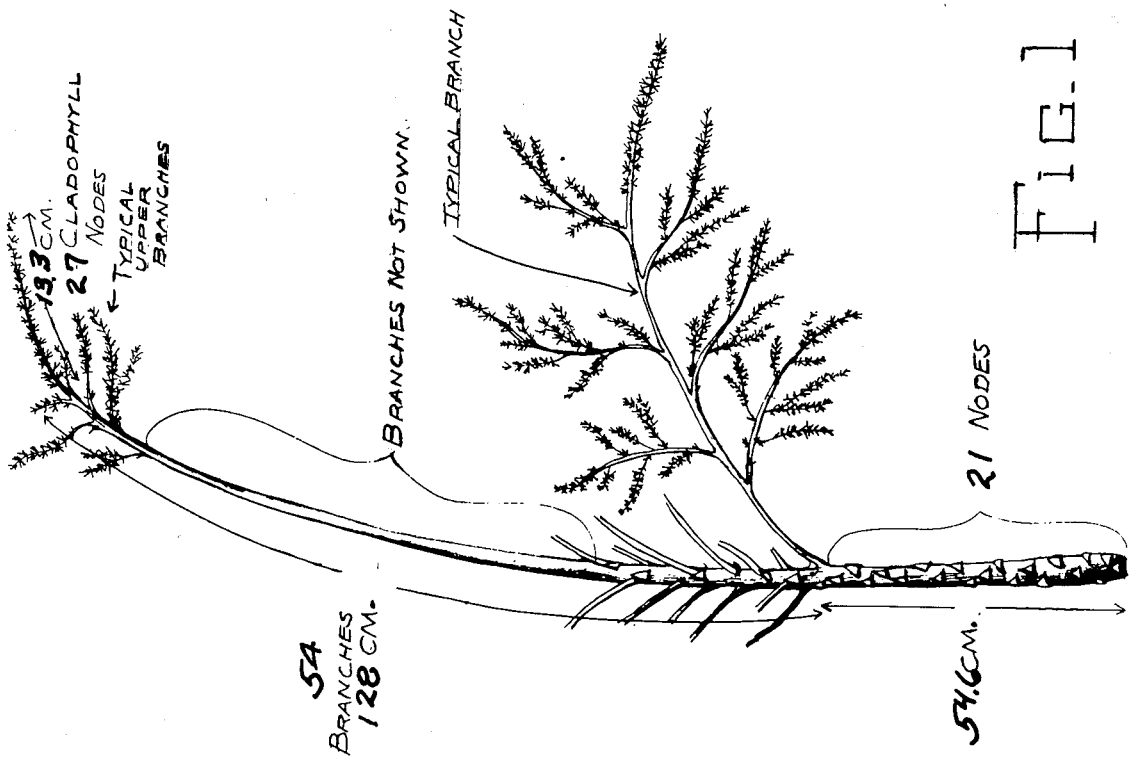

In order to illustrate and further disclose some of the aspects of our new Asparagus plant, we have prepared the data in the following table and in the drawing wherein FIG. 1, discloses some of that data as applied to a typical plant and in FIG. 2 a color illustration with colors as nearly representative of a typical plant as such an illustration can provide, the colors referring to Munsell Color Limit Cascade, by Macbeth Division of Kollmorgen Corp.

DETAILED BONTANICAL DESCRIPTION

| ASPARAGUS PLANT NO. JERSEY TITAN (277E × 22–8) | Inch × 2.54 = cm. |
|---|---|
| STALK DATA | |
| The specifications to follow are presented in centimeters unless otherwise indicated. The number "1", in parenthesis, indicates that measurements were taken from the largest stalk. | |
| Number of nodes below first branch(1) | 21 |
| Number of cm from crown to first branch(1) | 54.6 |
| Number of branches | 54 |
| Number cm. between first and last branch(1) | 128 |
| Internode length in cm. between branches(1) | 2.37 |
| Number of cladophyll nodes beyond last branch | 27 (1) |
| Number of cm. beyond last branch | 13.3 |
| Internode length in cm. beyond last branch | 0.49 (1) |
| Largest stalk diameter in mm | 14 |
| Mean diameter of three largest stalks in mm | 13.3 |
| Number of stalks | 13 |
| Stalk vigor index (No. × Mean Diam) | 2,300 |
| Mature stalk color, bloom removed(1) | 21–13 |
| Highest headed stalk cm to first branch | 54.6 |
| Length of highest headed stalk cm | 196.0 |
| FLOWER DATA | |
| Petal tip (yellow) | 26–4 |
| Petal base (purple) | 48–6 |
| Flower length mm | 6.72 |
| Flower width at midpoint mm | 2.53 |
| CLADOPHYLL DATA | |
| Number per node | 4.85 |
| Length mm | 10.5 |
| Width mm | 0.123 |

We claim:

1. A new and distinct variety of Asparagus plant as herein shown and described, characterized particularly as to novelty by the unique combination as an all male hybrid of production of high yield of marketable spears with tight spear tips in hot weather which remain closed longer than most cultivars, tolerance to rust (*Puccinia asparagi*), root rot (*Fusarium oxysporum*), and crown rot (*F. moniliforme*) of good vigor, and very high branching.

* * * * *